United States Patent
Wilson

(10) Patent No.: US 6,398,748 B1
(45) Date of Patent: Jun. 4, 2002

(54) SPLINT BANDAGE AND METHOD

(76) Inventor: Robert B. Wilson, 1 Edgewater La., South Hadley, MA (US) 01075

( * ) Notice: Subject to any disclaimer, the term of this patent is extended or adjusted under 35 U.S.C. 154(b) by 0 days.

(21) Appl. No.: 09/513,984

(22) Filed: Feb. 26, 2000

Related U.S. Application Data

(60) Provisional application No. 60/150,326, filed on Aug. 23, 1999, and provisional application No. 60/124,684, filed on Mar. 16, 1999.

(51) Int. Cl.⁷ .................................................. A61F 5/00
(52) U.S. Cl. ............................ 602/21; 602/5; 602/13; 602/20; 602/23; 128/869
(58) Field of Search ........................... 602/5, 6, 20, 21, 602/22, 27, 14, 64; 128/878, 869, 879, 881; 607/106, 109, 111, 112, 114

(56) References Cited

U.S. PATENT DOCUMENTS

| | | |
|---|---|---|
| 3,176,685 A | 4/1965 | Shamrook |
| 3,326,211 A | 6/1967 | Logue et al. |
| 4,136,686 A | 1/1979 | Arluck |
| 4,539,793 A * | 9/1985 | Malek |
| 4,541,885 A * | 9/1985 | Caudill, Jr. |
| 4,854,309 A | 8/1989 | Elsey |
| 5,415,624 A | 5/1995 | Williams |
| 5,713,837 A | 2/1998 | Grim et al. |
| 5,772,620 A | 6/1998 | Szlema et al. |
| 5,910,126 A * | 6/1999 | Wilson et al. ............... 602/75 |
| 6,039,909 A * | 3/2000 | Bernard et al. ............ 264/220 |
| 6,129,695 A * | 10/2000 | Peters et al. ................. 602/62 |

* cited by examiner

*Primary Examiner*—Michael A. Brown
*Assistant Examiner*—Lalita M. Hamilton
(74) *Attorney, Agent, or Firm*—Robert A. Seemann

(57) ABSTRACT

A non-radio frequency energy sensitive sheet shaped to cover a palm and wrist is wrapped over a radio frequency energy sensitive sheet, a splint, attachment strap first ends, and a rod configured to receive the other ends of the attachment straps around the rod, and radio frequency energy is injected into the wrap by a mold having non-radio frequency energy sensitive press walls kept below sheet melting temperature until the second sheet is fused to itself around the splint and around the rod and bonded to the first sheet by the radio frequency generated heat provided by the second sheet.

12 Claims, 6 Drawing Sheets

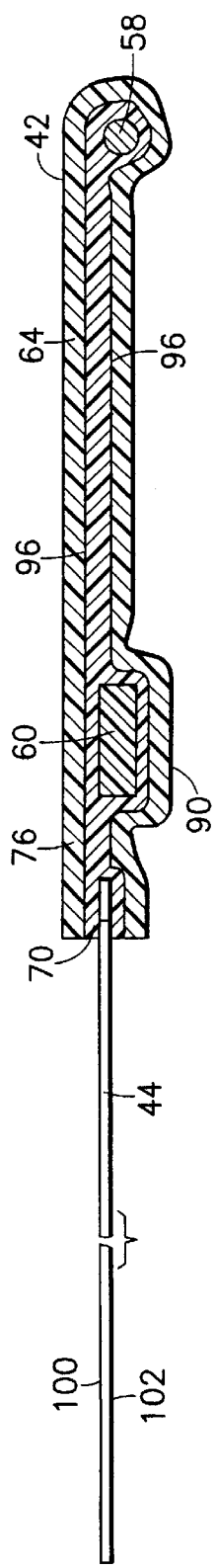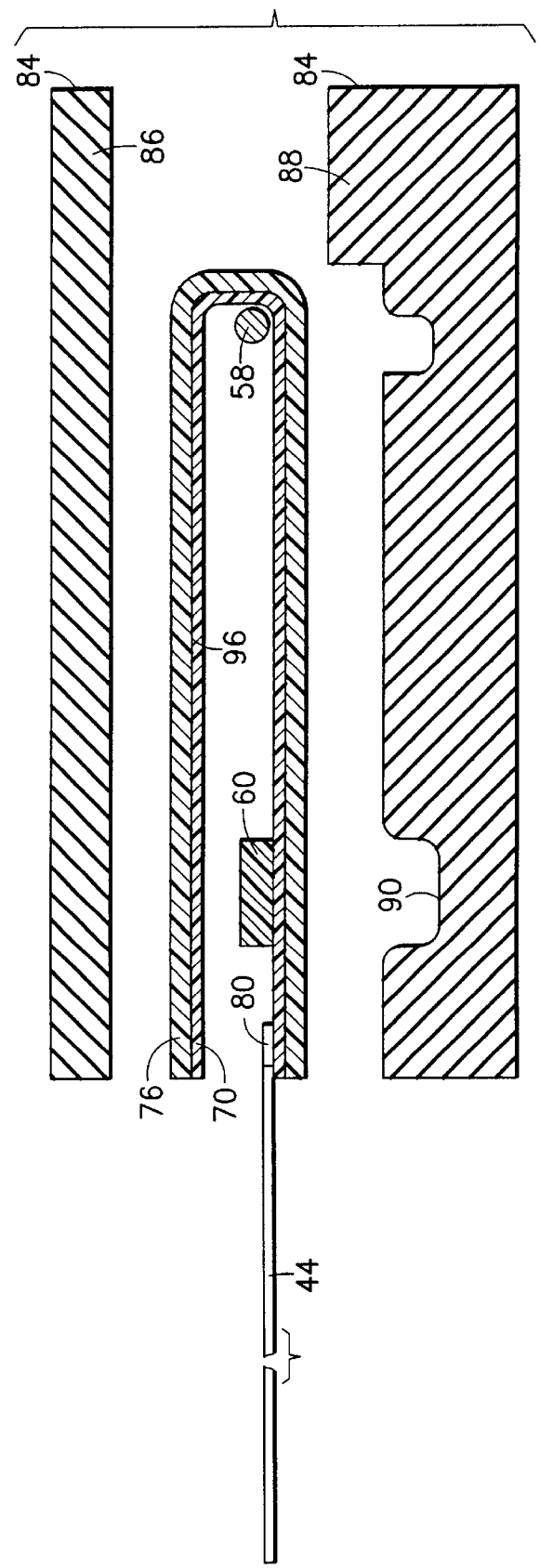

SPLINT BANDAGE AND METHOD

This application claims the benefit of U.S. Provisional Application No. 60/124,684, filed Mar. 16, 1999, and U.S. Provisional Application No. 60/150,326, filed Aug. 23, 1999.

BACKGROUND OF THE INVENTION

1. Field of the Invention

The invention relates to bandages, more specifically to an orthopedic splint appliance for a body part. The invention provides a bandage having, a permanent brace and fastening element formed within the bandage.

2. Description of the Prior Art

U.S. Pat. No. 4,854,309 patented Aug. 8, 1989 by D. Elsey describes a wrist splint comprising a flexible panel of a foam core between expandable skin layers, and pockets on the panel containing stays and having a foam core between expandable skin layers.

U.S. Pat. No. 5,415,624 patented May 16, 1995 by S. Williams describes an elasticized breathable wrap-around base material contoured to an anatomical part requiring treatment, releasable fastening means and an elasticized breathable pocket on the wrap-around material containing a liquid containing pod that is contoured to the shape of the anatomical part.

U.S. Pat. No. 5,713,837 patented Feb. 3, 1998 by Grim et al. describes an orthopedic support having a base made of a material of which flexibility is a function of thickness, molded in different thicknesses in one shot to provide thin areas of the wrap around support that are flexible and thicker areas that are rigid and provide splinting support.

SUMMARY OF THE INVENTION

It is one object of the invention to provide an appliance for a body part requiring a splint.

It is another object that the appliance can be economically and quickly custom designed for a particular area of the body part that requires the splint.

It is another object that the custom design of each appliance can be made permanent.

A first sheet shaped to cover a palm and a wrist, which is not sensitive to radio frequency energy at a frequency at which the appliance is molded so that the first sheet does not significantly heat and does not soften when it is exposed to the radio frequency energy, is wrapped over a second sheet which is sensitive to radio frequency energy at the frequency at which the appliance is molded so that the second sheet heats and softens when it is exposed to the radio frequency energy, and the first sheet is wrapped, second sheet inward, over a splint, and wrapped over a rod, and then radio frequency energy is applied to the to the wrapping until the second sheet is fused to itself around the splint and around the rod, and bonded to the first sheet by the radio frequency generated heat provided by the second sheet, and radio frequency sensitive material of the appliance melts from heat generated by the material into tubelets in a wall of the mold forming hooks for a book and loop fastener.

BRIEF DESCRIPTION OF THE DRAWINGS

In order that the invention be more fully comprehended, it will now be described, by way of example, with reference to the accompanying drawings, in which:

FIG. 4 is a cross section view of the appliance of FIG. 2 taken along 4—4.

FIG. 5 is a cross section view of the appliance of FIG. 4 in a mold prior to molding.

DESCRIPTION OF THE PREFERRED EMBODIMENTS

Figure 1:
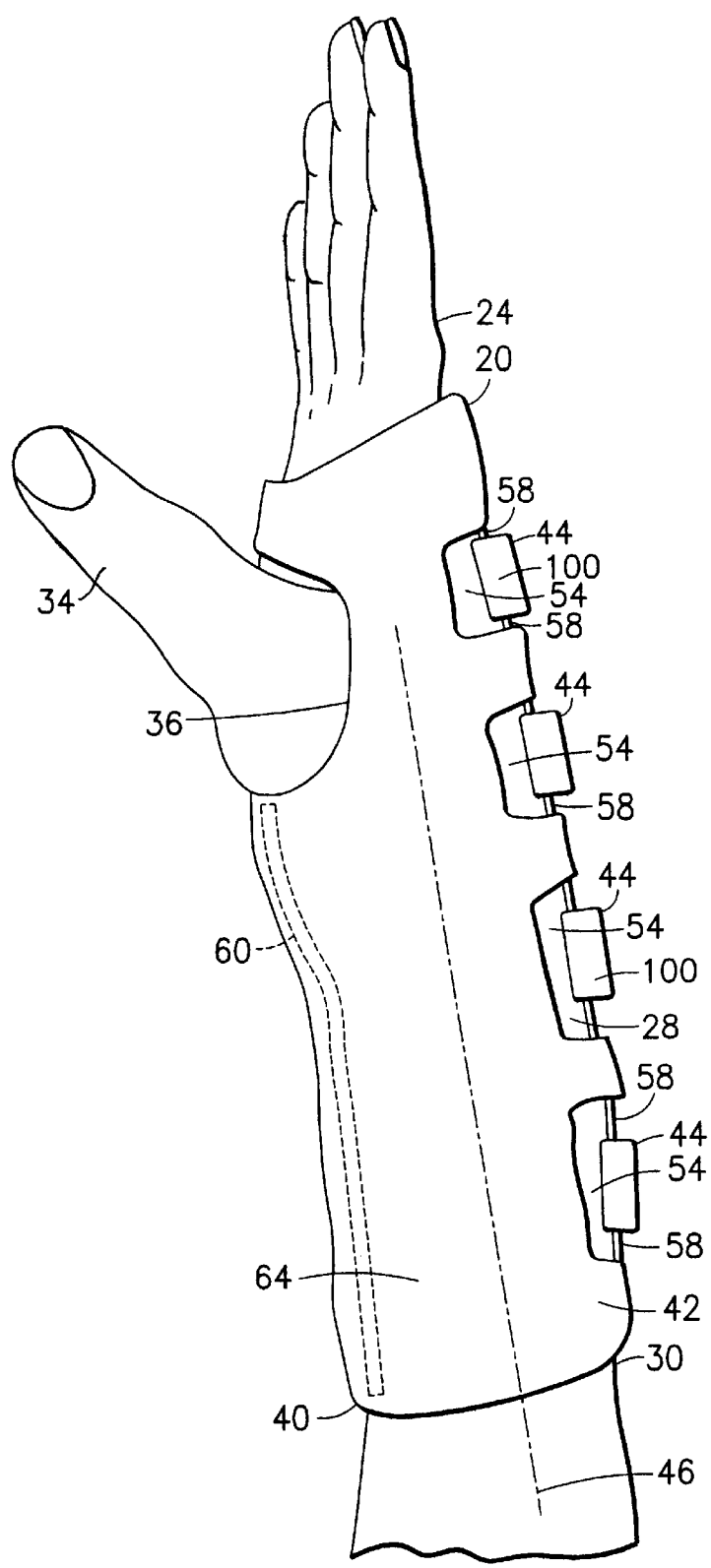
FIG. 1 is a perspective view of a hand wearing an appliance of the present invention.

Before explaining the invention in detail, it is to be understood that the invention is not limited in its application to the detail of construction and arrangement of parts illustrated in the drawings since the invention is capable of other embodiments and of being practiced or carried out in various ways. It is also to be understood that the phraseology or terminology employed is for the purpose of description only and not of limitation.

In this specification, the word "tubelet" and its plural "tubelets" represents the elements that were spelled "tublets" for the plural in U.S. provisional application No. 60/150,326 filed Aug. 23, 1999.

Figure 2:
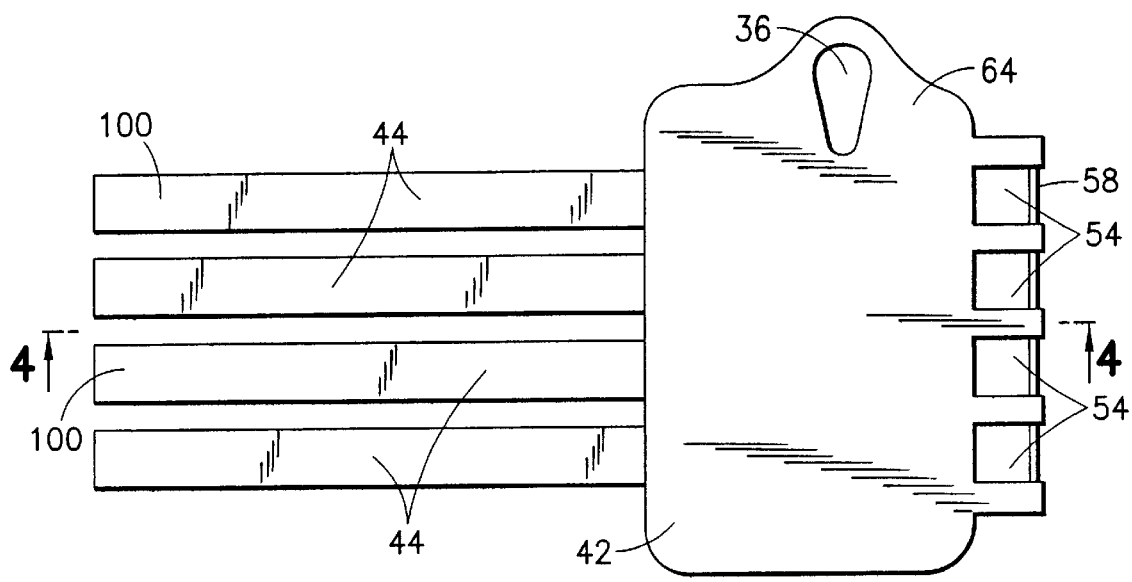
FIG. 2 is a front view of the appliance of FIG. 1, viewed toward the palm of a hand as it would be resting open on the palm of the hand.
Figure 3:
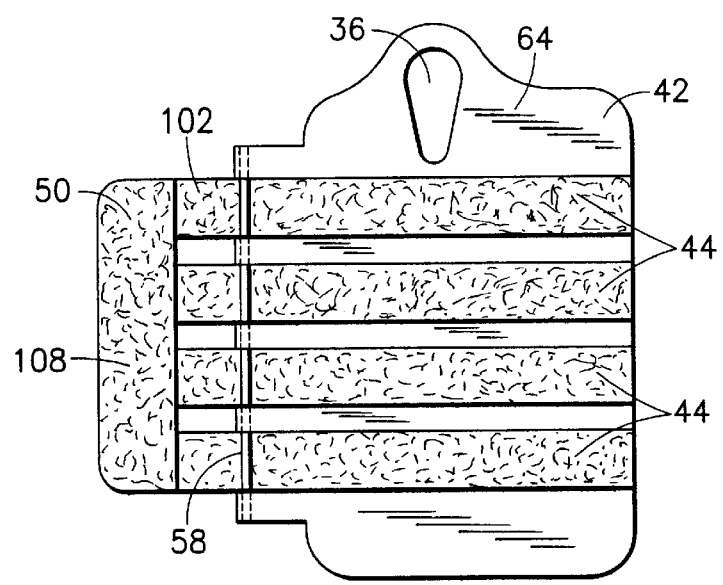
FIG. 3 is a back view of the appliance of FIG. 1 with the straps folded over the back of the appliance under a flexible bar of the invention.
Figure 6:
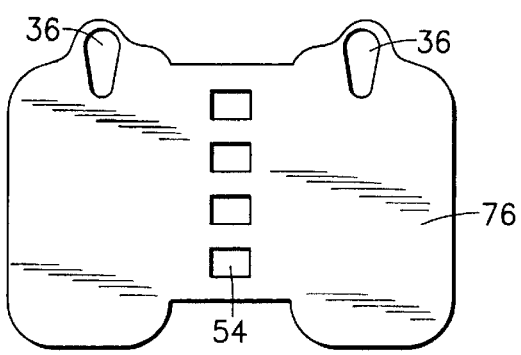
FIG. 6 is a front view of a sheet of the appliance of FIG. 4 which is not responsive to radio frequency energy at a molding frequency.
Figure 7:
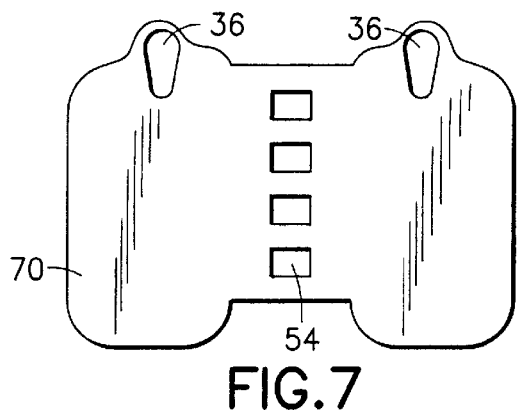
FIG. 7 is a front view of a sheet of the appliance of FIG. 4 which is responsive to radio frequency energy at the molding frequency.
Figure 8:
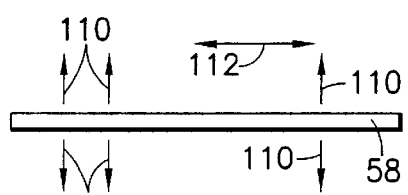
FIG. 8 is a top view of a flexible bar of the appliance of FIG. 4.
Figure 9:
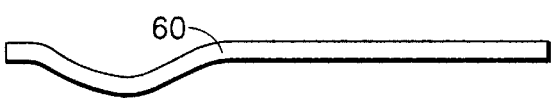
FIG. 9 is an enlarged side view of a palm/wrist splint of the appliance of FIG. 4.
Figure 11:
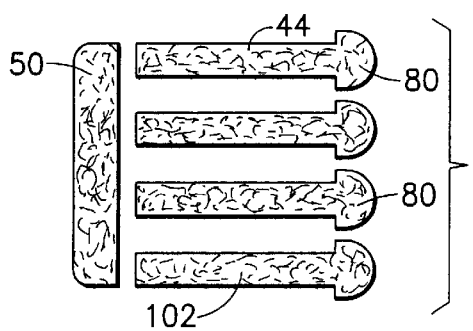
FIG. 11 is a reduced back view of straps of the appliance of FIG. 4.
Figure 10:
FIG. 10 is a top view of the palm/wrist splint of FIG. 9.
Figure 12:
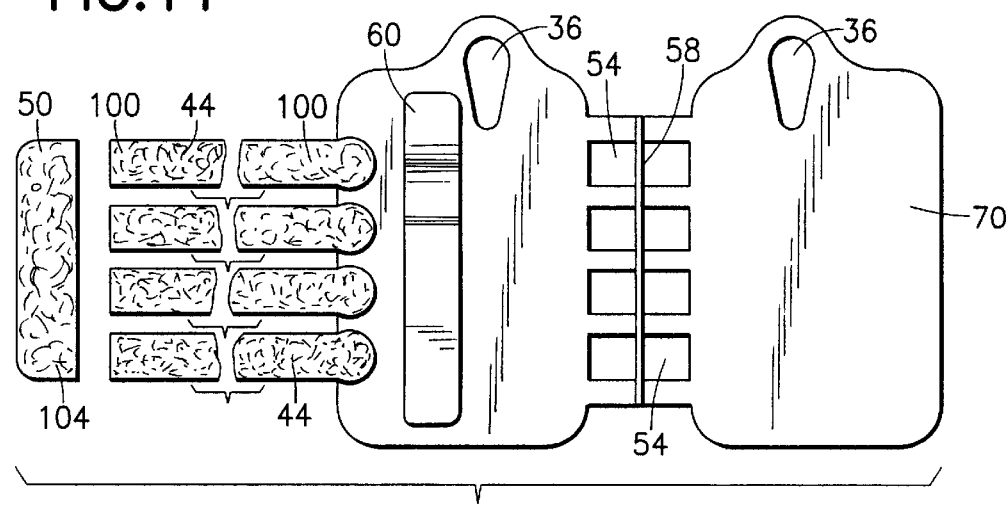
FIG. 12 is a planar schematic view of the appliance of FIG. 4 before it is folded. The radio frequency responsive sheet of FIG. 7 is shown. The sheet of FIG. 6 is not shown, as it is behind the radio frequency responsive sheet.

Referring to FIGS. 1, 2, and 3, appliance 20 is wrapped around hand 24 and wrist 28 of limb 30. Thumb 34 passes through hole 36 in shell 40.

Shell 40 is made by wrapping bandage 42 panel 64 around the hand and wrist, drawing bandage 42 straps 44 across the back of the hand and wrist, and fastening the straps to themselves by strip 50. Strip 50 uses a hook and loop fastening system. A hook and loop fastening system entitled Velcro (™) is suitable.

Straps 44 pass through openings 54, around flexible rod 58, and back over themselves. Rod 58 is round in cross section. It can be elliptical, square, or any shape in cross section so long as it provides strong support against lateral pull of the straps generally normal to longitudinal axis 46. Preferably the surface of the rod is shaped so that the straps can slide over the surface as they are being drawn tight.

In FIG. 2 the straps are not yet passed through openings 54. Strip 50 is applied to the ends of the straps after they are passed through openings 54. Strip 50 may be applied permanently to the straps or may be removably attached to them by hook and loop system surfaces such as Velcro (™) surfaces.

Preferably sufficient length of strap is provided so that a hand can be inserted between the straps and bandage panel 64 when the bandage is in the configuration of FIG. 3.

Splint 60 is contained within bandage 42, incorporated into the bandage during the molding process of the bandage. The splint is preferably reinforced plastic, but can be metal or other material. It is shaped to fit the palm and wrist to best support them for relief of carpal tunnel syndrome.

Referring to FIGS. 4–12, FIG. 4 shows the appliance after it is molded. FIG. 5 shows a radio frequency press used to mold the appliance from elements shown in FIGS. 6–11 which are arranged in FIG. 12 for folding and molding in the press of FIG. 5.

Die cut sheet 70 is sensitive to radio frequency energy at a predetermined frequency so that it heats and softens when it is exposed to the radio frequency energy.

Die cut sheet 76 is not sensitive to radio frequency energy at the predetermined frequency so that it does not significantly heat and does not soften when it is exposed to the radio frequency energy.

In FIG. 5 sheet 76 is wrapped over sheet 70 and folded over rod, 58, plint 6 an be-shaped ends 80 of straps 44.

Mold 84 walls 86, 88, are made of a material which preferably is not sensitive to the radio frequency energy so that it does not heat from direct exposure to the radio frequency. One material which may be used is silicone rubber.

The folded sheets are pressed between walls 86, 88 while radio :frequency energy is applied to the elements between the walls. This results in molded bandage 42 having the shape received from the design 90 formed in walls 86, 88.

Mold walls 86, 88, are preferably kept at temperatures below the softening temperature of the bandage materials.

Sheet 76 may be made of cotton, polypropylene, polyester, or any material which has the described radio frequency response for sheet 76. Sheet 76 may be woven or embossed plastic.

Preferably a layer of foam padding having the radio frequency response characteristics described for sheet 76 is included between sheet 76 and sheet 70. This foam may be an integral part of sheet 76 prior to the assembly of sheet 76 with sheet 70.

Sheet 70 may be made of vinyl, urethane, or any material which has the described radio frequency response for sheet 70.

Sheet 70 bonds to itself by fusion, and to sheet 76, and to straps 44 by melting to them.

Preferably sheet 76 side 96 is textured or porous toward sheet 70, for example by way of the surface of the integral foam, so that sheet 70 extends into the surface of sheet 76.

One of sides 100 and 102 of straps 44 is preferably responsive to the radio frequency energy and softens or fuses with sheet 70.

Side 102 has interspersed hooks and loops so that it sticks to itself when folded over onto itself.

Strip 50 side 104 is attached to the ends of the straps with Velcro (™) on its back side, and is attached to the straps on fold-over by hooks or loops or both hooks and loops on its front side 108.

Strip 50 can be attached to the ends of the straps by melting by radio frequency energy and bonding to the straps.

Rod 58 flexes laterally 110, resiliently, along its length 112 so that shell 40 is drawn snugly to the hand and wrist by the straps which are drawn in unison at their ends by strip 50.

Figure 13:
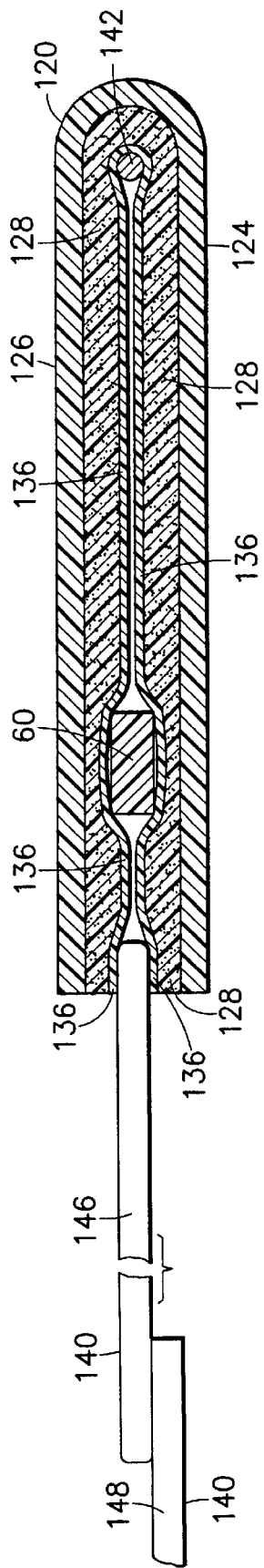
FIG. 13 is a cross section view of another appliance of the invention.

Referring to FIG. 13, in appliance 120, sheet 124 of bandage panel 126 includes integrally attached foam layer 128. Sheet 124 and the foam is not sensitive to radio frequency energy at the predetermined frequency used in molding the appliance.

Coating 136 on foam layer 128 is sensitive to radio frequency energy at the predetermined frequency so that it heats and softens when it is exposed to the radio frequency energy. In the molding process, coating 136 is melted by the radio frequency energy. It melts to itself, to strap 140, and preferably to splint 60 and rod 142.

Strap 140 attaches to itself like strap 44 described earlier. Elastic portion 146 is in-line with Velcro (™) attachment portion 148.

Elastic portion 146 stretches, varying the length of the strap so that the shell formed by the bandage is drawn snugly to the hand and wrist by the straps.

Rod 142 is stiff, but may be made flexible to supplement the elastic yield provided by the elastic straps.

Figure 14:
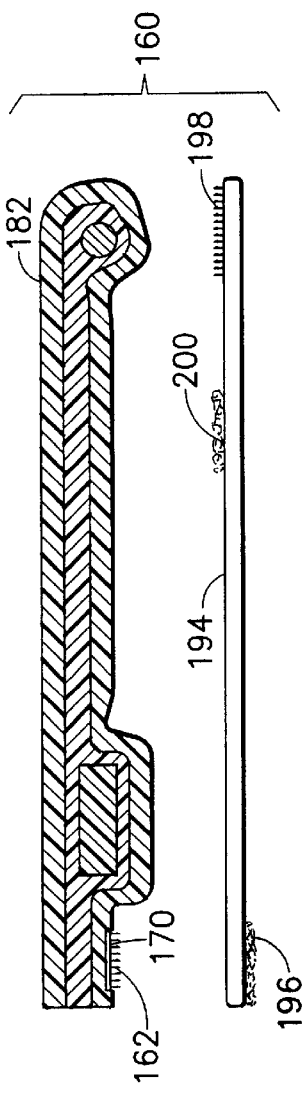
FIG. 14 is a cross section view of another appliance of the invention.

Referring to FIG. 14, appliance 160 includes integrally molded hooks 162 for hook and loop fastening to strap 194 that contains the loops 196 on one end of the strap. The strap also contains hooks 198 and loops 200 on other parts of the strap so that it can be used to tighten the appliance on a hand. Preferably the strap is passed around rod 58 like straps 44 of appliance 20.

Figure 15:
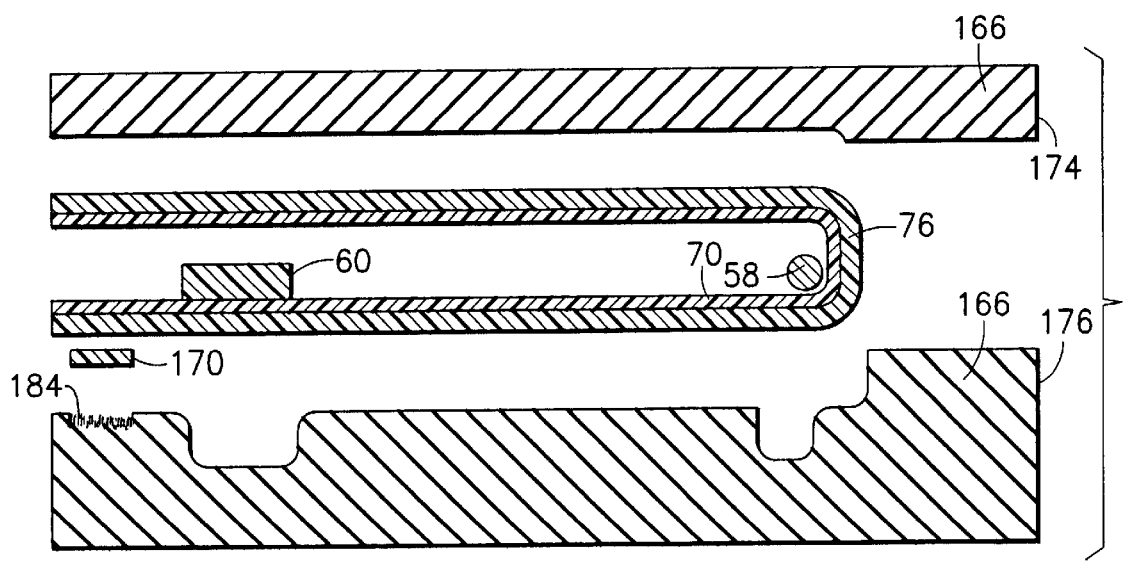
FIG. 15 is a cross section view of the appliance of FIG. 14 in an open mold prior to molding.

In FIG. 15, elements 70, 76, 58, and 60 are assembled in mold 166 as described above for bandage 42 in mold 84.

Strip 170 is flat and extends along the length of the appliance from the wrist end to the finger end so that it can be contacted by a plurality of straps 194 that go across the appliance cross wise to the longitudinal axis of the appliance like appliance 20.

Strip 170 can be a single elongated element, or a plurality of elements, that are square, round or have other shapes, that are configured on the bandage to attach the plurality of straps 194 to the bandage.

Strip 170 is sensitive to radio frequency energy at a predetermined frequency so that it heats and softens when it is exposed to radio frequency energy. Preferably strip 170 is sensitive to the radio frequency energy at the frequency that is used to melt sheet 70.

Mold 166 walls 174, 176 are made of a material that is not sensitive to the radio frequency energy and are kept at temperatures below the softening temperature of the bandage 182 comprising elements 70, 76, 58, 60, and 170.

Figure 16:
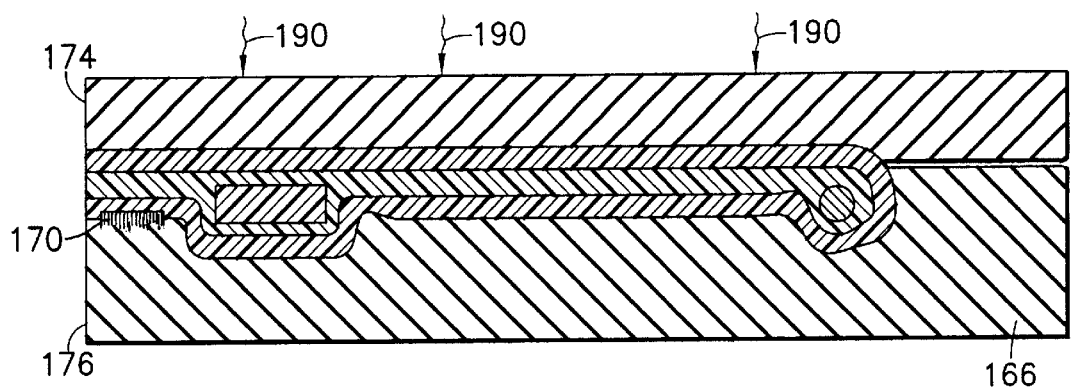
FIG. 16 is a cross section view of the appliance of FIG. 15 in the closed mold.

In FIG. 16 mold 166 walls 174, 176 are forcibly pressed together by hydraulic or other means, and radio frequency energy 190 is applied to the bandage through the mold. Sheet 70 melts as described above for bandage 42.

Strip 170 also softens or melts sufficiently to bind to or flow into the weave of sheet 76, and flow into tubelets 184 in the upper surface of wall 176, forming thereby hooks of a hook and loop fastener when the plastic of strip 170 cools and bandage 182 is stripped from the mold.

Mold wall 176 is preferably made of silicon rubber in, which the tubelets were formed by molding them in the silicon from a master comprising a fastener hook surface.

Figure 17:
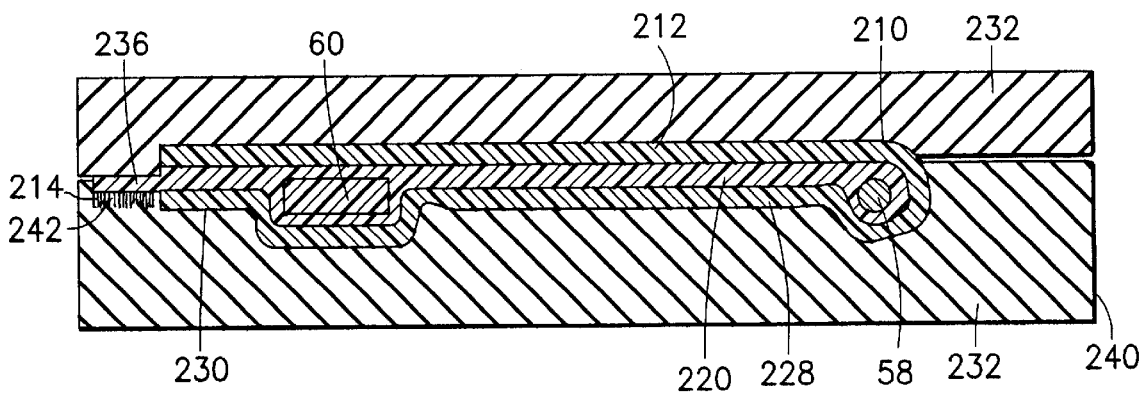
FIG. 17 is a cross section view of another appliance of the invention in a closed mold.

In FIG. 17 appliance 210 bandage 212, integrally molded hooks 214 for hook and loop fastening to straps are formed by sheet 220 that is sensitive to radio frequency energy at a predetermined frequency so that it heats and softens whin it is exposed to radio frequency energy. Sheet 220 is folded to itself, enclosing splint 60, and rod 58.

Sheet 228 is not sensitive to radio frequency energy at the predetermined frequency so that it does not significantly heat and soften when it is exposed to the radio frequency energy.

Cavity 230 of silicon rubber mold 232 is extended to receive end 236 of folded sheet 220 which is longer than folded sheet 228 as shown in cross section in FIG. 17.

Wall 240 of the mold includes tubelets 242 to receive sheet 220 when sheet 220 melts to itself, around splint 60, around rod 58, to sheet to sheet 228, and into tubelets 242 from the heat that sheet 220 generates from the radio frequency energy that it receives when the radio frequency energy at the predetermined frequency is delivered to the mold.

It is seen from the above that an apparatus of the invention can be custom designed and manufactured for a particular body area requiring a splint, with permanently affixed splint, and hook and loop fastener means, by setting, folding and molding, economically and quickly.

Although the present invention has been described with respect to details of certain preferred embodiments thereof, it is not intended that such details be limitations upon the scope of the invention. It will be obvious to those skilled in the art that various modifications and substitutions may be made without departing from the spirit and scope of the invention as set forth in the following claims.

What is claimed is:

1. A molded appliance for a body part having a front, a back, and an area requiring a splint, said appliance comprising:
   a first sheet which is not sensitive to radio frequency energy at a radio frequency at which the appliance is molded so that said first sheet does not significantly heat and does not soften when said first sheet is exposed to the radio frequency energy, shaped to cover at least said area,
   a splint,
   a second sheet which is sensitive to radio frequency energy at the radio frequency at which the appliance is molded so that said second sheet heats and softens when it is exposed to the radio frequency energy, fused to itself around said splint and around a rod, and bonded to said first sheet by the radio frequency generated heat provided by said second sheet,
   hooks for hook and loop fastening, extending from said appliance, formed from said second sheet by radio frequency generated heat provided by said second sheet when said second sheet is fused to itself.

2. A molded appliance for a body part having a front, a back, and an area requiring a splint, said appliance comprising:
   a first sheet which is not sensitive to radio frequency energy at a radio frequency at which the appliance is molded so that said first sheet does not significantly heat and does not soften when said first sheet is exposed to the radio frequency energy, shaped to cover at least said area,
   a splint,
   a second sheet which is sensitive to radio frequency energy at the radio frequency at which the appliance is molded so that said second sheet heats and softens when it is exposed to the radio frequency energy, fused to itself around said splint and around a rod, and bonded to said first sheet by the radio frequency generated heat provided by said second sheet,
   at least one hole through said second sheet adjacent to said rod for receiving means for fastening said appliance on said body part.

3. The molded appliance of claim 2 wherein said rod is flexible.

4. The molded appliance of claim 2 wherein said rod is resiliently flexible.

5. The molded appliance of claim 2 further comprising:
   a strap surrounded at one end by said second sheet,
   at least one of the hook and a loop, of a hook and loop fastener system on a first side of said strap.

6. The molded appliance of claim 5, further comprising:
   said strap comprising an elastic portion.

7. A molded appliance for a body part having a front, a back, and an area requiring a splint, said appliance comprising:
   a first sheet which is not sensitive to radio frequency energy at a radio frequency at which the appliance is molded so that said first sheet does not significantly heat and does not soften when said first sheet is exposed to the radio frequency energy, shaped to cover at least said area,
   a splint,
   a second sheet which is sensitive to radio frequency energy at the radio frequency at which the appliance is molded so that said second sheet heats and softens when it is exposed to the radio frequency energy, fused to itself around said splint and around a rod, and bonded to said first sheet by the radio frequency generated heat provided by said second sheet,
   a strap surrounded at one end by said second sheet,
   interspersed hooks and loops of a hook and loop fastener system on a first side of said strap, said strap is configured so that said first side sticks to itself when wrapped around said rod and brought to itself over the back of said body part when the first sheet is over the front of said body part.

8. A molded appliance for a body part having an area requiring a splint, said appliance comprising:
   a first sheet which is not sensitive to radio frequency energy at a radio frequency at which the appliance is molded so that said first sheet does not significantly heat and does not soften when said first sheet is exposed to the radio frequency energy, shaped to cover at least said area,
   a splint,
   a first layer on said first sheet, that is sensitive to radio frequency energy at the radio frequency at which the appliance is molded so that said first layer heats and softens when it is exposed to the radio frequency energy, fused to itself around said splint by the radio frequency generated heat provided by said first layer,
   a rod, said first layer is fused to itself and around said rod,
   at least one hole through said first layer adjacent to said rod for receiving means for fastening said appliance on said body part.

9. The molded appliance of claim 8 further comprising:

hooks for hook and loop fastening, extending from said appliance, formed from a first element fused to said appliance, that is sensitive to radio frequency energy at the frequency at which the appliance is molded so that said first element heats and softens when it is exposed to the radio frequency energy, the forming of said hooks and the bonding of said first element to said appliance being by radio frequency generated heat provided by said first element when said first layer is fused to itself.

10. The molded appliance of claim 8 further comprising:

a strap surrounded at one end of said strap by said first layer.

11. A method for making an appliance for a body part having an area requiring a splint, said method comprising:

wrapping a first layer of material which is not sensitive to radio frequency energy at a frequency at which the appliance is molded so that said first layer does not significantly heat and does not soften when said first layer is exposed to the radio frequency energy, shaped to cover at least said area, and a second layer of material which is sensitive to radio frequency energy at the frequency at which the appliance is molded so that said second layer heats and softens when said second layer is exposed to the radio frequency energy, over a splint and a rod spaced from said splint, wrapping said second layer around said rod so that said second layer folds back into contact with itself between said rod and said splint and applying radio frequency energy to the wrapping in a mold that forms the appliance until said second layer is fused to itself around said splint and said rod by the radio frequency generated heat provided by said second layer.

12. The method of claim 11, further comprising:

inserting material of said second layer into hook shaped tubelets in a wall of said mold that forms the appliance when the radio frequency energy is applied to the mold to fuse the second layer to itself around said splint simultaneously with forming hooks for a hook and loop fastener from said second layer.

* * * * *